United States Patent
Bristow

(10) Patent No.: US 11,229,206 B2
(45) Date of Patent: Jan. 25, 2022

(54) FUNGICIDAL COMPOSITION

(71) Applicant: JIANGSU ROTAM CHEMISTRY CO., LTD, Jiangsu (CN)

(72) Inventor: James Timothy Bristow, Chai Wan (HK)

(73) Assignee: JIANGSU ROTAM CHEMISTRY CO., LTD, Jiangsu (CN)

( * ) Notice: Subject to any disclaimer, the term of this patent is extended or adjusted under 35 U.S.C. 154(b) by 63 days.

(21) Appl. No.: 16/613,603

(22) PCT Filed: May 8, 2018

(86) PCT No.: PCT/CN2018/085964
§ 371 (c)(1),
(2) Date: Nov. 14, 2019

(87) PCT Pub. No.: WO2018/210158
PCT Pub. Date: Nov. 22, 2018

(65) Prior Publication Data
US 2020/0100501 A1 Apr. 2, 2020

(30) Foreign Application Priority Data
May 16, 2017 (EP) .................................... 17171416

(51) Int. Cl.
| A01N 43/653 | (2006.01) |
| A01N 37/34 | (2006.01) |
| A01P 3/00 | (2006.01) |
| A01N 25/32 | (2006.01) |

(52) U.S. Cl.
CPC ........... *A01N 43/653* (2013.01); *A01N 25/32* (2013.01); *A01N 37/34* (2013.01); *A01P 3/00* (2021.08)

(58) Field of Classification Search
CPC ....................................................... A01P 3/00
See application file for complete search history.

(56) References Cited

U.S. PATENT DOCUMENTS

| 4,937,261 A * | 6/1990 | Wilde ..................... A01N 59/20 514/479 |
| 5,789,430 A * | 8/1998 | Jautelat ................. C07D 249/12 514/384 |
| 6,521,628 B1 * | 2/2003 | Cotter .................... A01N 35/04 514/258.1 |
| 2010/0216825 A1 | 8/2010 | Haas et al. |
| 2011/0195841 A1 | 8/2011 | Dittgen et al. |
| 2016/0106105 A1 | 4/2016 | Dutzmann et al. |
| 2016/0360751 A1 | 12/2016 | Oliveira et al. |

FOREIGN PATENT DOCUMENTS

| CN | 102885054 A | 1/2013 |
| EP | 1776864 A1 | 4/2007 |
| GN | 102640748 A | 8/2012 |
| WO | 2015079334 A1 | 6/2015 |
| WO | 2016207182 A1 | 12/2016 |

OTHER PUBLICATIONS

Webster's New World Dictionary, The World Publishing Co., New York, p. 1127 (1972).*
Machine translation of CN 102885054 (Jan. 2013).*
Derwent abstract 2013-G30145; abstracting CN 102885054 (Jan. 2013).*
International Search Report and Written Opinion regarding Application No. PCT/CN2018/085964 dated Jul. 24, 2018.
European Search Report regarding EP 17171416.5 dated Jul. 12, 2017.
Simon Oxley: Appropriate Fungicide Dose Curve Generator—About the Fungicides, Jun. 6, 2006, p. 1, XPO55390015.
Dr. Simon Oxley: Home-Grown Cereals Authority Ramularia Leaf Spot in Barley, Topic Sheet 97/Summer 2007, Jul. 1, 2007, pp. 1-3, XP955389985.
S J P Oxley, et al.: Understanding Fungicide Mixtures to Control Rhynchosporium in Barley and Minimise Resistance Shifts, Home-Grown Cereals Authority (HGCA), Project Report 436, Aug. 5, 2008, pp. 1-6, XPO55389986.
A. K. Culbreath, et al., Management of Leaf Spot Diseases of Peanut with Prothioconazole Applied Alone or in Combination with Tebuconazole orTrifloxystrobin, Peanut Science(2008)35:149-158, pp. 167-176.
Fandango, All You Need in One Fungicide-Guide to Effective Use; www.bayercropscience.co.uk/fandango, Mar. 2005, pp. 231-243.
Dr. Simon Oxley, Home-Grown Cereals Authority, Topic Sheet 97/SUMMER 2007, Ramularia Leaf Spot in Barley, pp. 244-246.
Form 7A (Pre-Grant Representation) in respect of Patent Application No. IN201917048332 dated Jun. 24, 2020.
Dupont: "Aylora/Treoris in spring barley", DuPont Crop Protection Products Product Guide 2016, Feb. 1, 2016, pp. 1-383, XP055389988 (18 pages attached).
Chinese First Office Action with translation corresponding to Application No. 201880005389.5 dated Jan. 11, 2021.

* cited by examiner

*Primary Examiner* — John Pak
(74) *Attorney, Agent, or Firm* — Dickinson Wright PLLC

(57) ABSTRACT

A fungicidal composition is provided, the composition comprising:
  Component (A): prothioconazole; and
  Component (B): chlorothalonil.
There is also provided a method for the control and/or prevention of fungal infestations in a plant, the method comprising applying to the plant, plant parts or the locus thereof:
  Component (A): prothioconazole; and
  Component (B): chlorothalonil.
The combination of prothioconazole and chlorothalonil exhibits synergy and also exhibits a reduction in phytotoxicity.

5 Claims, No Drawings

FUNGICIDAL COMPOSITION

CROSS REFERENCE TO RELATED APPLICATIONS

This is a US National Phase application based upon PCT Application No. PCT/CN2018/085964, filed May 8, 2018. This application claims the priority of European Patent Application No. 17171416.5, filed May 16, 2017 and titled "FUNGICIDAL COMPOSITION", and the disclosures of which are hereby incorporated by reference.

FIELD

The present invention concerns a fungicidal composition. The composition may be used for preventing and/or treating fungal infestations in plants and plant parts. The present invention also relates to a method of preventing and/or treating fungal infestations in plants and plant parts.

BACKGROUND

Undesired fungal infection in crop plants causes significant yield reduction. Therefore, the control of the undesired fungal infection is crucial to obtain high productivity in crops and is a continual objective in the agricultural field.

Chlorothalonil, having the IUPAC name tetrachloroisophthalonitrile, has the following structural formula (I):

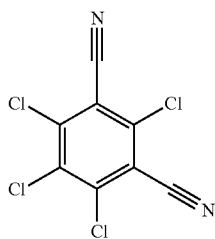

(I)

Chlorothalonil belongs to the chloronitrile fungicide group of compounds, which are used as fungicides, in particular to control a range of fungal diseases including late leaf spot, leaf spot, rust, web blotch, septoria leaf spot, septoria leaf spot, early blight, potato blight, seedling blight, leaf blight, brown spot and downy mildew in a wide range of crops, including pome fruit, stone fruit, citrus fruit, bush and cane fruit, cranberries, strawberries, pawpaws, bananas, mangoes, coconut palms, oil palms, rubber, pepper, vines, hops, vegetables, cucurbits, tobacco, coffee, tea, rice, soya beans, peanuts, potatoes, sugar beet, cotton, maize, ornamentals, mushrooms, and turf. Chlorothalonil is a non-systemic foliar fungicide acting by the conjugation with and depletion of thiols (particularly glutathione) from germinating fungal cells, leading to disruption of glycolysis and energy production, inducing fungistasis.

Prothioconazole, having the IUPAC name 2-[2-(1-chlorocyclopropyl)-3-(2-chlorophenyl)-2-hydroxypropyl]-2,4-dihydro-1,2,4-triazole-3-thione, has the following structural formula (II):

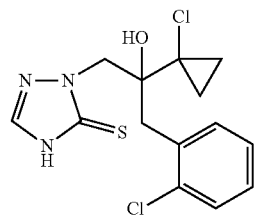

(II)

Prothioconazole is a synthetic compound of the triazole family of compounds, which are a class of systemic fungicides that enter the plant and spread from the site of application to untreated or newly grown area, uprooting existing fungi and/or protecting the plant from future fungal infestations. The mechanism of action of prothioconazole is due to its ability to interfere with the biosynthesis of biosteroids or to inhibit the biosynthesis of ergosterol. Ergosterol is needed by the fungus for membrane structure and function and is essential for the development of functional cell walls. The application of prothioconazole in abnormal fungal growth and eventually death.

Chlorothalonil has been found to cause phytotoxic damage to a range of plants, such as grapes, apples and flowering ornamentals, such as miniature rose and *Pittosporum*.

"Phytotoxicity" in the context of the present invention relates to any effect of a fungicide that hinders the ordinary development of a plant, in particular the plants targeted for protection from fungal infestation, such as crop plants. Phytotoxic effects of a fungicide may reduce the growth of the plant and may even cause its death. Therefore, a fungicide having high activity against fungal infestations while exhibiting a low, preferably zero, phytotoxic effect is desirable to maintain healthy crop plants.

SUMMARY

It has now surprisingly been found that combining chlorothalonil with prothioconazole results in a reduction of the phytotoxic effects of chlorothalonil and prothioconazole on a range of plants, particularly crop plants such as grape, miniature rose, *Pittosporum* and apple, without reducing effectiveness in the control of the undesired fungal infestation. The phytotoxic effects of prothioconazole can also be reduced by combination with chlorothalonil. In addition, it has been found that a combination of prothioconazole and chlorothalonil exhibits a fungicidal activity significantly greater than that expected from the activity two components employed separately. That is, the combination of prothioconazole and chlorothalonil exhibit synergy.

According to a first aspect of the present invention there is provided a fungicidal composition comprising:
Component (A): prothioconazole; and
Component (B): chlorothalonil.

In a further aspect, the present invention provides a method for the control and/or prevention of fungal infestations in a plant comprising applying to the plant, plant parts or the locus thereof:
Component (A): prothioconazole; and
Component (B): chlorothalonil.

In still further aspect, the present invention provides the use of a combination of:
Component (A): prothioconazole; and
Component (B): chlorothalonil in the control and/or prevention of a fungal infestation of a plant.

In a yet further aspect, the present invention provides the use of prothioconazole to reduce the phytotoxicity of chlorothalonil to plants.

In a still further aspect, the present invention provides the use of chlorothalonil to reduce the phytotoxicity of prothioconazole to plants.

The present invention also provides a method of reducing the phytotoxicity of chlorothalonil, the method comprising using chlorothalonil in combination with prothioconazole.

The present invention further provides a method of reducing the phytotoxicity of prothioconazole, the method comprising using prothioconazole in combination with chlorothalonil.

The compositions of the present invention comprise a combination of (A) prothioconazole and (B) chlorothalonil. In certain preferred embodiments, the total amount of the component (A) prothioconazole and the component (B) chlorothalonil present in the composition is from 5% to 99% by weight, preferably 10% to 90%, more preferably 20% to 80% by weight of the fungicidal composition.

Component (A) prothioconazole may be present in the composition in an amount of at least 0.5% by weight, preferably from 1% by weight, up to 70% by weight, preferably up to 65%, more preferably up to 60%, still more preferably up to 55%, especially up to 50% by weight. The composition may comprises (A) prothioconazole in an amount of from 0.5 to 60% by weight, preferably from 0.5 to 55%, more preferably from 1 to 50% by weight.

Component (B) chlorothalonil may be present in the composition in an amount of at least 0.5% by weight, preferably from 1% by weight, more preferably from 2%, up to 70% by weight, preferably up to 65%, more preferably up to 60%, still more preferably up to 55%, especially up to 50% by weight. The composition may comprises (B) chlorothalonil in an amount of from 0.5 to 60% by weight, preferably from 1 to 55%, more preferably from 2 to 50% by weight.

The compositions of the present invention may be produced in conventional manner and provided in any suitable formulation, for example by mixing component (A) prothioconazole and component (B) chlorothalonil, together with one or more auxiliaries appropriate for the type of formulation.

The auxiliaries employed in the composition will depend upon the type of formulation and/or the manner in which the formulation is to be applied by the end user. Formulations incorporating the composition of the present invention are described hereinafter. Suitable auxiliaries which may be comprised in the composition according to the invention are all customary formulation adjuvants or components, such as extenders, carriers, solvents, surfactants, stabilizers, anti-foaming agents, anti-freezing agents, preservatives, antioxidants, colorants, thickeners, solid adherents and inert fillers. Such auxiliaries are known in the art and are commercially available. Their use in the formulation of the compositions of the present invention will be apparent to the person skilled in the art.

Formulation types suitable for the compositions of the present invention include water-soluble concentrates (SL), emulsifiable concentrates (EC), oil-in-water emulsions (EW), micro-emulsions (ME), suspension concentrates (SC), oil-based suspension concentrates (OD), flowable concentrates (FS), water-dispersible granules (WG), water-soluble granules (SG), wettable powders (WP), water soluble powders (SP), granules (GR), encapsulated granules (CG), fine granules (FG), macrogranules (GG), aqueous suspo-emulsions (SE), capsule suspensions (CS) and microgranules (MG). The following paragraphs will describe the exemplary formulations of the fungicide composition including water-dispersible granules (WG), aqueous suspension concentrates (SC), emulsifiable concentrates (EC), and water-soluble concentrates (SL).

The fungicidal composition may comprise one or more inert fillers. Such inert fillers are known in the art and available commercially. Suitable fillers include, for example, natural ground minerals, such as kaolins, aluminas, talc, chalk, quartz, attapulgite, montmorillonite, and diatomaceous earth, or synthetic ground minerals, such as highly dispersed silicic acid, aluminum oxide, silicates, and calcium phosphates and calcium hydrogen phosphates. Suitable inert fillers for granules include, for example, crushed and fractionated natural minerals, such as calcite, marble, pumice, sepiolite, and dolomite, or synthetic granules of inorganic and organic ground materials, as well as granules of organic material, such as sawdust, coconut husks, corn cobs, and tobacco stalks.

The fungicidal compositions of the present invention optionally include one or more surfactants, which are preferably non-ionic, cationic and/or anionic in nature, and surfactant mixtures which have good emulsifying, dispersing and wetting properties, depending on the nature of the active compound to be formulated. Suitable surfactants are known in the art and are commercially available.

The surfactant can be an emulsifier, dispersant or wetting agent of ionic or nonionic type. Examples which may be used are salts of polyacrylic acids, salts of lignosulphonic acid, salts of phenylsulphonic or naphthalenesulphonic acids, polycondensates of ethylene oxide with fatty alcohols or with fatty acids or with fatty amines, substituted phenols, especially alkylphenols, sulphosuccinic ester salts, taurine derivatives, especially alkyltaurates, or phosphoric esters of polyethoxylated phenols or alcohols. The presence of at least one surfactant is generally required when the active compound and/or the inert carrier and/or auxiliary/adjuvant are insoluble in water and the vehicle for the final application of the composition is water.

Examples of suitable surfactants are polyoxyethylated (POE) sorbitan esters, such as POE (20), sorbitan trioleate and polyoxyethylated (POE) sorbitol esters, such as POE (40), sorbitol hexaoleate. POE (20) sorbitan trioleate is commercially available under the tradenames ATLAS G1086 and CIRRASOL G1086 marketed by UniqEMA. Further examples of suitable surfactants are the alkali metal salts of alkylnaphthalene sulfonates, with sodium alkyl naphthalene sulfonate-formaldehyde condensate, such as MORWET® EFW, being particularly suitable for compositions of the present invention. The surfactant may also include condensates of alkali metal alkylnaphthalene-sulfonates with aldehydes, such as MORWET® D-425. Combinations of a POE sorbitan ester with a POE sorbitol ester allow the HLB (hydrophilic-lipophilic balance) value of the surfactant to be optimized, so as to obtain the highest quality emulsion (smallest suspended droplets) when the composition is added to water. Higher quality of emulsions typically leads to optimal fungicidal performance.

Suitable anionic surfactants can be both so-called water-soluble soaps and water-soluble synthetic surface-active compounds. Soaps which may be used in the composition are the alkali metal, alkaline earth metal or substituted or unsubstituted ammonium salts of higher fatty acid ($C_{10}$ to $C_{22}$), for example the sodium or potassium salt of oleic or stearic acid, or of natural fatty acid mixtures.

The amount of surfactant present in the composition will depend upon such factors as the type of formulation employed.

The fungicidal compositions of the present invention optionally further comprise one or more polymeric stabilizers. The suitable polymeric stabilizers that may be used in the present invention include, but are not limited to, polypropylene, polyisobutylene, polyisoprene, copolymers of monoolefins and diolefins, polyacrylates, polystyrene, polyvinyl acetate, polyurethanes or polyamides. Suitable stabilizers are known in the art and commercially available.

The surfactants and polymeric stabilizers mentioned above are generally believed to impart stability to the composition, in turn allowing the composition to be formulated, stored, transported and applied.

Suitable anti-foam agents include all substances which can normally be used for this purpose in agrochemical compositions. Suitable anti-foam agents are known in the art and are available commercially. Particularly preferred anti-foam agents are mixtures of polydimethylsiloxanes and perfluroalkylphosphonic acids, such as the silicone anti-foam agents available from GE or Compton.

Suitable organic solvents that may be used in the compositions may be selected from all customary organic solvents, which thoroughly dissolve one or more of the active compounds employed. Again, suitable organic solvents for the active compounds in the compositions of the present invention are known in the art. The following may be mentioned as being preferred: N-methyl pyrrolidone, N-octyl pyrrolidone, cyclohexyl-1-pyrrolidone; or a mixture of paraffinic, isoparaffinic, cycloparaffinic and aromatic hydrocarbons, such as SOLVESSO™200. Suitable solvents are commercially available.

Suitable preservatives include all substances which can normally be used for this purpose in agrochemical compositions of this type and again are well known in the art. Suitable preservatives that may be mentioned include tolylfluanid, such as Preventol® (available commercially from Bayer AG), and benzisothiazolinone, such as Proxel® (available commercially from Bayer AG).

Suitable antioxidants are all substances which can normally be used for this purpose in agrochemical compositions, as is known in the art. Preference is given to butylated hydroxytoluene.

Suitable thickeners include all substances which can normally be used for this purpose in agrochemical compositions. Suitable thickeners include, for example xanthan gum, PVOH, cellulose and its derivatives, clay hydrated silicates, magnesium aluminum silicates or a mixture thereof. Again, such thickeners are known in the art and available commercially.

The fungicidal composition of the present invention may further comprise one or more solid adherents. Such adherents are known in the art and are available commercially. They include organic adhesives, including tackifiers, such as celluloses or substituted celluloses, natural and synthetic polymers in the form of powders, granules, or lattices, and inorganic adhesives, such as gypsum, silica, or cement.

In addition, depending upon the formulation, the composition according to the invention may also comprise water.

The combination of components (A) prothioconazole and (B) chlorothalonil, for example in the composition of the present invention, can be employed in crop plants to control fungal infestations of plants, including crop plants. As indicated above, the action of chlorothalonil is to reduce the phytotoxicity of prothioconazole. As also indicated above, prothioconazole also acts to reduce the phytotoxicity of chlorothalonil.

The combination of components (A) prothioconazole and (B) chlorothalonil may be used to protect a wide range of plants. In particular, the combination may be used to protect a range of crop plants from fungal infestations. Crop plants that may be treated using the present invention include cereals, such as wheat, barley, rye, oats, rice, maize, sorghum, millet and manioc; beet, such as sugar beet and fodder beet; fruit, such as pomes, stone fruit and soft fruit, such as apples, pears, plums, peaches, almonds, cherries, or berries, for example, strawberries, raspberries and blackberries; leguminous plants, such as beans, lentils, peas and soybeans; oil plants, such as rape, mustard, poppy, olives, sunflowers, coconut, castor oil plants, cocoa beans and groundnuts; cucurbitaceae, such as marrows, cucumbers and melons; fibrous plants, such as cotton, flax, hemp and jute; citrus fruit, such as oranges, lemons, grapefruit and mandarins; vegetables, such as spinach, lettuce, asparagus, cabbages, carrots, onions, tomatoes, potatoes and paprika; lauraceae, such as avocados, cinnamon and camphor; and tobacco, nuts, coffee, aubergines, sugar cane, tea, pepper, vines, hops, bananas, natural rubber plants, eucalyptus, as well as ornamental plants.

Especially preferred plants for treatment using the present invention are stone fruit, vines and ornamental plants and fruit. Particularly preferred crop plants are grape, miniature rose, *Pittosporum* and apple.

The fungicidal compositions and method of the present invention are effective in controlling a wide range of undesired fungal infestations, including, but not limited to infestations of: *Sphaerotheca* spp., *Colletotrichum* spp., *Venturia* spp., *Alternaria* spp., *Cercospora* spp., *Mycosphaerella* spp., *Puccinia* spp., *Pythium* spp., *Typhula* spp., *Drechslera* spp., *Mycoleptodiscus terrestris*, *Phakopsora pachyrhizi*, *Diaporthe phaseolorum*, *Diaporthe phaseolorum* var. *caulivora*, *Phomopsis phaseoli* [anamorph], *Erysiphe graminis*, *Sphaerotheca fuliginea*, *Pseudoperonospora cubensi*, *Phytophthora infestans*, *Alternaria solani*, *Alternaria tenuissima*, *Leptosphaeria nodorum*, *Septoria tritici*, *Pyrenophora teres*, *Cladosporium carpophilum*, *Mycosphaerella arachidis*, *Rhizoctonia solani*, *Microdochium nivale*, *Bipolaris sorokiniana*, *Gloeocercospora sorghi*, *Colletotrichum graminicola*, *Puccinia graminis*, *Pyricularia grisea*, *Venturia inaequalis*, *Laetisaria fuciformis* and *Sclerotium rolfsii*.

In general, the weight ratio of prothioconazole to chlorothalonil used in the aspects of the present invention can be in the range of from 1:50 to 10:1, preferably from 1:30 to 1:1, more preferably from 1:25 to 1:1. It is preferred that chlorothalonil is employed in a weight amount in excess of the weight amount of prothioconazole, that is the weight ratio of prothioconazole to chlorothalonil is less than 1:1. Preferably, the weight ratio of prothioconazole to chlorothalonil is from 1:5 to 1:25, more preferably from 1:10 to 1:20. More preferably, the weight ratio of prothioconazole to chlorothalonil is from 1:12 to 1:16, more preferably still from 1:13 to 1:15, with a particularly effective weight ratio being from 1:14 to 1:14.5, especially from 1:14 to 1:14.5, in particular 1:14.1.

In the method and use of the present invention, prothioconazole with chlorothalonil may be applied in any desired sequence or in any combination, for example consecutively or simultaneously. Co-application of the prothioconazole with the chlorothalonil can be achieved by obtaining from a separate formulation source and mixing together (known as a tank-mix, ready-to-apply, spray broth, or slurry), optionally with other pesticides, such as other fungicides, insecticides and nematicides, or by obtaining from a single formulation mixture source (known as a pre-mix, concentrate, formulated compound (or product)), and optionally mixing together with other pesticides, such as other fungicides, insecticides and nematicides. In one embodiment, the method and use of the present invention employ a composition according to the present invention.

In general, the application rate of the fungicidal composition depends on the specific active ingredient in the combination, type of weed, type of crop plant, soil type, season, climate, soil ecology and various other factors. The application rate of the composition for a given set of conditions can readily be determined by trials.

The application rate of the total amount of component (A) prothioconazole and component (B) chlorothalonil may be in the range of from 10 to 3000 grams of active ingredients per hectare (g/ha), preferably from 50 to 2500 g/ha, more preferably from 100 to 2000 g/ha.

In certain embodiments, the application rate of prothioconazole is in the range of from 10 to 300 g/ha, preferably from 15 to 250 g/ha, more preferably from 20 to 200 g/ha, even more preferably from 40 to 120 g/ha. Specific examples of application rates for prothioconazole are 47 g/ha, 75 g/ha and 103 g/ha.

In certain embodiments, the application rate of chlorothalonil is in the range of from 100 to 2500 g/ha, preferably from 200 to 2000 g/ha, more preferably from 300 to 1800 g/ha, even more preferably from 500 to 1500 g/ha. Examples of specific application rates for chlorothalonil are 663 g/ha, 1080 g/ha and 1440 g/ha.

The components (A) prothioconazole; and (B) chlorothalonil may be applied to the plants to be protected, parts of the plants, including seeds thereof, and/or to the locus of the plants, including the locus into which the plants or parts thereof are to be sown or planted.

The components (A) prothioconazole; and (B) chlorothalonil may each be applied to the plants, parts thereof of their locus once or a plurality of times, for example two, three or four times, over a period of time, such as one, two or more days.

DETAILED DESCRIPTION

The aspects of the present invention are further described, for illustration purposes only, by way of the following working examples.

Unless stated otherwise, percentages are weight percent.

Formulation Examples

The following formulation examples illustrate the compositions of the present invention.

The compositions of Examples 1 to 14 and the Control are summarized in Table 1 below. The compositions summarized in Table 1 were prepared as follows.

Water-dispersible Granule (WG)

Water-dispersible granule (WG) formulations were prepared by intimately mixing finely ground components (A) and (B) in the amounts indicated in Table 1 with auxiliaries, grinding through superfine mill and then granulating by paste extrusion to obtain water-dispersible granules. The auxiliaries included 2% w/w of MORWET® EFW powder (sodium alkylnaphthalene sulfonate and anionic surfactant), 5% w/w of MORWET® D-425 powder (sodium alkylnaphthalenesulfonate-formaldehyde condensate), 1% w/w of AGNIQUE® L soap (fatty acids, tallow, sodium salts) and mannitol (balance to 100%).

For use, the water-dispersible granules were diluted with water to the desired concentration of active ingredients.

Aqueous Suspension Concentrate (SC)

Aqueous suspension concentrate (SC) formulations were prepared by mixing finely ground prothioconazole and chlorothalonil with auxiliaries, which included 8% w/w of propylene glycol, 0.5% w/w of SAG 1529 (modified polydimethylsiloxane), 3% w/w of MORWET® D-425 powder (sodium alkylnaphthalenesulfonate-formaldehyde condensate), 2% w/w of ATLAS™ G-5000 (polyalkylene glycol ether), 0.2% of AG-RHO POL 23/W (xanthan gum), 0.1% w/w of NIPACIDE BIT 20 (1,2-Benzisothiazol-3-one) and water (balance to 100%).

In Table 1 below, the formulations of Examples 1 to 8 are embodiments of the present invention. The remaining formulations are presented for comparison purposes only.

TABLE 1

| Example No. | Formulation type | Active ingredient (A) prothioconazole (%) | Active ingredient (B) chlorothalonil (%) | Ratio (A):(B) | Application rate (g/ha) (A) prothioconazole | (B) chlorothalonil |
|---|---|---|---|---|---|---|
| 1 | WG | 1 | 50 | 1:50 | 50 | 2500 |
| 2 | SC | 1 | 30 | 1:30 | 50 | 1500 |
| 3 | SC | 2 | 40 | 1:20 | 72 | 1440 |
| 4 | WG | 2 | 28.2 | 1:14.1 | 47 | 663 |
| 5 | SC | 3 | 30 | 1:10 | 108 | 1080 |
| 6 | SC | 4 | 20 | 1:14.1 | 94 | 1326 |
| 7 | WG | 30 | 3 | 10:1 | 400 | 40 |
| 8 | SC | 20 | 20 | 1:1 | 400 | 400 |
| 9 | SC | 36 | 0 | / | 72 | 0 |
| 10 | SC | 47 | 0 | / | 47 | 0 |
| 11 | WG | 47 | 0 | / | 94 | 0 |
| 12 | WG | 0 | 40 | / | 0 | 1440 |
| 13 | SC | 0 | 28.2 | / | 0 | 663 |
| 14 | WG | 0 | 28.2 | / | 0 | 1326 |
| Control | SC | | 0 | / | 0 | 0 |

Biological Examples

The following biological examples were conducted using the formulations summarized in Table 1 above.

A combination of two or more active compounds has synergistic effect when the efficacy of the combination of two or more active compounds is greater than the sum of the efficacy of each active compound when applied individually.

The expected activity for a given combination of two active compounds can be calculated by the "Colby equation" (S. R. Colby, Weeds 15, 20-22, 1967), as follows:

$$E = A + B - (A \times B / 100)$$

where:
A=the percent efficacy of compound A when compound A is employed at a dose of m (gram per hectare, i.e. g/ha);
B=the percent efficacy of compound B when compound B is employed at a dose of n (g/ha);
E=the percent estimated efficacy when compounds A and B are employed together at a dose of m (g/ha) and n (g/ha), respectively.

Example 1

Phytoxicity

The following tests were conducted to investigate the phytotoxicity to target plants of the compositions summarized in Table 1 above.

Grape, apple, miniature rose and *Pittosporum* plants were planted in beds of good agricultural peat based growth medium and grown in separate greenhouses. After the plants had emerged and grown to a height of about 4 inches, separate beds of the plants were sprayed with one of the compositions of Examples 1 to 14 and the Control at the application rates (g ai/ha) indicated in Table 1. After treatment, the beds were maintained for about 1 week under greenhouse conditions conducive for good plant growth.

Visual ratings of phytotoxicity were made after 1 week. Phytotoxicity was ranked 0 to 5, where 5 indicates severe phytotoxicity (leaves and stems showed severe yellowing, burning, or necrosis) and 0 indicated no phytotoxicity.

The results are set forth below in Table 2.

TABLE 2

| | Phytotoxicity Ranking (1-5) | | | |
|---|---|---|---|---|
| Example No. | Grape | Apple | miniature rose | *Pittosporum* |
| 1 | 5 | 4.5 | 4 | 4 |
| 2 | 4 | 3.5 | 3 | 3.5 |
| 3 | 1 | 1 | 0.5 | 1.5 |
| 4 | 0.5 | 0.5 | 0 | 0.5 |
| 5 | 3 | 3.5 | 3 | 2.5 |
| 6 | 0.5 | 0.5 | 0 | 1 |
| 7 | 3.5 | 4 | 3.5 | 3.5 |
| 8 | 4.5 | 3.5 | 4.5 | 4.5 |
| 9 | 2 | 2 | 2 | 2 |
| 10 | 1.5 | 1.5 | 1.5 | 2 |
| 11 | 2 | 2 | 2.5 | 3 |
| 12 | 4 | 5 | 4.5 | 5 |
| 13 | 3 | 4.5 | 3 | 4 |
| 14 | 4 | 3.5 | 4.5 | 4.5 |
| Control | 0 | 0 | 0 | 0 |

The results set out in Table 2 above show that combining chlorothalonil with prothioconazole significantly reduces the phytotoxicity of chlorothalonil to the treated plants. Similarly, the phytotoxic effects exhibited by prothioconazole when used alone are reduced when chlorothalonil is present. The reduction in phytotoxicity is particularly marked at a weight ratio of prothioconazole to chlorothalonil of from 1:10 to 1:20, in particular, the compositions of Examples 3, 4 and 6.

Example 2

Fungicidal Activity on Grape-Downy Mildew (*Plasmopara Viticola*)

Soybean plants were sprayed with a conidial suspension of *plasmopara viticola* and incubated at conditions of 20° C. and 100% relative atmospheric humidity for 48 hours. The plants were then sprayed with compositions prepared according to Examples 3, 4, 6, 9, 10, 11, 12, 13, 14 and Control formulation as set out in Table 1 above.

Thereafter, the treated plants were held in a greenhouse at conditions of 15° C. and 80% relative atmospheric humidity for 10 days, after which the severity of the fungal infestation was assessed. The efficacy of the composition in treating the fungal infestation was then determined.

The results of the efficacy of the fungicidal compositions are set out in Table 3 below.

TABLE 3

| | | Application rate (g/ha) | | | |
|---|---|---|---|---|---|
| Example No. | Ratio (A):(B) | (A) prothioconazole | (B) chlorothalonil | Efficacy | Expected efficacy |
| 3 | 1:20 | 72 | 1440 | 90 | 56 |
| 4 | 1:14.1 | 47 | 663 | 95 | 28 |
| 6 | 1:14.1 | 94 | 1326 | 98 | 47.5 |
| 9 | / | 72 | 0 | 20 | / |
| 10 | / | 47 | 0 | 10 | / |
| 11 | / | 94 | 0 | 25 | / |
| 12 | / | 0 | 1440 | 45 | / |
| 13 | / | 0 | 663 | 20 | / |
| 14 | / | 0 | 1326 | 30 | / |
| Control | / | 0 | 0 | 0 | / |

The results set out in Table 3 above show that the combination of prothioconazole and chlorothalonil exhibits a significantly improved effect in the treatment of plants infested with grape-downy mildew, compared with the activity of prothioconazole and chlorothalonil applied individually, and a significantly greater effect than that expected from the performance of the two active compounds when used alone. This indicates that the combination of prothioconazole and chlorothalonil exhibits a significant synergy in the control of grape-downy mildew.

Example 3

Fungicidal Activity on Rose Powdery Mildew (*Sphaerotheca Pannosa Var. Rosae*)

Miniature rose plants were sprayed with a conidial suspension of *Sphaerotheca pannosa* var. *rosae* and incubated at conditions of 20° C. and 100% relative atmospheric humidity for 48 hours. The plants were then sprayed with compositions of the formulations in Examples 3, 4, 6, 9, 10, 11, 12, 13, 14 and the Control set out in Table 1 above.

Thereafter, the treated plants were held in a greenhouse at conditions of 15° C. and 80% relative atmospheric humidity for 10 days, after which the severity of the fungal infestation was assessed. The results of the efficacy of the fungicidal compositions of the different formulations are set out in the Table 4 below.

TABLE 4

| Example No. | Ratio (A):(B) | Application rate (g/ha) | | Efficacy | Expected efficacy |
| | | (A) prothioconazole | (B) chlorothalonil | | |
| --- | --- | --- | --- | --- | --- |
| 3 | 1:20 | 72 | 1440 | 92 | 65 |
| 4 | 1:14.1 | 47 | 663 | 94 | 40.5 |
| 6 | 1:14.1 | 94 | 1326 | 98 | 64 |
| 9 | / | 72 | 0 | 30 | / |
| 10 | / | 47 | 0 | 15 | / |
| 11 | / | 94 | 0 | 40 | / |
| 12 | / | 0 | 1440 | 50 | / |
| 13 | / | 0 | 663 | 30 | / |
| 14 | / | 0 | 1326 | 40 | / |
| Control | / | 0 | 0 | 0 | / |

The results set out in Table 4 above show that the combination of prothioconazole and chlorothalonil exhibits a significantly improved effect in the treatment of plants infested with rose powdery mildew, compared with the activity of prothioconazole and chlorothalonil applied individually, and a significantly greater effect than that expected from the performance of the two active compounds when used alone. This indicates that the combination of prothioconazole and chlorothalonil exhibits a significant synergy in the control of rose powdery mildew.

Example 4

Fungicidal Activity on Apple Scab (*Venturia inaequalis*)

Apple (Pink Lady) plants were sprayed with a conidial suspension of *Venturia inaequalis* and incubated at conditions of 20° C. and 100% relative atmospheric humidity for 48 hours. The plants were then sprayed with compositions of the formulations in Examples 3, 4, 6, 9, 10, 11, 12, 13, 14 and the Control set out in Table 1.

Thereafter, the treated plants were held in a greenhouse at conditions of 15° C. and 80% relative atmospheric humidity for 10 days, after which the severity of the fungal infestation was assessed. The results of the efficacy of the fungicidal compositions of the different formulations are set out in the Table 5 below.

TABLE 5

| Example No. | Ratio (A):(B) | Application rate (g/ha) | | Efficacy | Expected efficacy |
| | | (A) prothioconazole | (B) chlorothalonil | | |
| --- | --- | --- | --- | --- | --- |
| 3 | 1:20 | 72 | 1440 | 95 | 68 |
| 4 | 1:14.1 | 47 | 663 | 92 | 37 |
| 6 | 1:14.1 | 94 | 1326 | 95 | 62.5 |
| 9 | / | 72 | 0 | 20 | / |
| 10 | / | 47 | 0 | 10 | / |
| 11 | / | 94 | 0 | 25 | / |
| 12 | / | 0 | 1440 | 60 | / |
| 13 | / | 0 | 663 | 30 | / |
| 14 | / | 0 | 1326 | 50 | / |
| Control | / | 0 | 0 | 0 | / |

The results set out in Table 5 above show that the combination of prothioconazole and chlorothalonil exhibits a significantly improved effect in the treatment of plants infested with apple scab, compared with the activity of prothioconazole and chlorothalonil applied individually, and a significantly greater effect than that expected from the performance of the two active compounds when used alone. This indicates that the combination of prothioconazole and chlorothalonil exhibits a significant synergy in the control of apple scab.

Example 5

Fungicidal Activity on Alternaria Leafspot—(*Alternaria tenuissima*)

*Pittosporum* plants were sprayed with a conidial suspension of *Alternaria tenuissima* and incubated at conditions of 20° C. and 100% relative atmospheric humidity for 48 hours. The plants were then sprayed with compositions of the formulations in Examples 3, 4, 6, 9, 10, 11, 12, 13, 14 and the Control set out in Table 1.

Thereafter, the treated plants were held in a greenhouse at conditions of 15° C. and 80% relative atmospheric humidity for 10 days, after which the severity of the fungal infestation was assessed. The results of the efficacy of the fungicidal compositions of the different formulations are set out in the Table 6 below.

TABLE 6

| Example No. | Ratio (A):(B) | Application rate (g/ha) | | Efficacy | Expected efficacy |
| | | (A) prothioconazole | (B) chlorothalonil | | |
| --- | --- | --- | --- | --- | --- |
| 3 | 1:20 | 72 | 1440 | 92 | 66 |
| 4 | 1:14.1 | 47 | 663 | 95 | 46 |
| 6 | 1:14.1 | 94 | 1326 | 98 | 64 |
| 9 | / | 72 | 0 | 15 | / |
| 10 | / | 47 | 0 | 10 | / |
| 11 | / | 94 | 0 | 20 | / |
| 12 | / | 0 | 1440 | 60 | / |
| 13 | / | 0 | 663 | 40 | / |
| 14 | / | 0 | 1326 | 55 | / |
| Control | / | 0 | 0 | 0 | / |

The results set out in Table 6 above show that the combination of prothioconazole and chlorothalonil exhibits a significantly improved effect in the treatment of plants infested with alternaria leafspot, compared with the activity of prothioconazole and chlorothalonil applied individually, and a significantly greater effect than that expected from the performance of the two active compounds when used alone. This indicates that the combination of prothioconazole and chlorothalonil exhibits a significant synergy in the control of alternaria leafspot.

The invention claimed is:

1. A method for the control of fungal infestations in a plant comprising applying a composition to a plant, plant parts or the locus thereof, wherein the composition comprises:
   Component (A): prothioconazole; and
   Component (B): chlorothalonil,
wherein the weight ratio of component (A) prothioconazole and component (B) chlorothalonil is 1:14.1.

2. The method according to claim 1, wherein the application rate of the total amount of component (A) prothioconazole and component (B) chlorothalonil is in the range of from 10 to 3000 grams of active ingredients per hectare (g/ha).

3. The method according to claim 1, wherein the application rate of prothioconazole is in the range of from 10 to 300 g/ha.

4. The method according to claim 1, wherein the application rate of chlorothalonil is in the range of from 100 to 2500 g/ha.

5. A method of reducing the phytotoxicity of chlorothalonil, comprising combining chlorothalonil with prothioconazole and applying the chlorothalonil and prothioconazole to a plant, plant parts or the locus thereof, wherein the weight ratio of prothioconazole and chlorothalonil is 1:14.1.

* * * * *